United States Patent [19]

Hazar

[11] Patent Number: 4,583,947
[45] Date of Patent: * Apr. 22, 1986

[54] CUSTOM DENTURES AND METHOD OF MAKING SAME

[75] Inventor: Mitchell M. Hazar, Scottsdale, Ariz.

[73] Assignee: Hazco Development Inc., Tempe, Ariz.

[*] Notice: The portion of the term of this patent subsequent to Sep. 11, 2001 has been disclaimed.

[21] Appl. No.: 542,039

[22] Filed: Oct. 14, 1983

Related U.S. Application Data

[63] Continuation-in-part of Ser. No. 476,233, Mar. 17, 1983, Pat. No. 4,470,815.

[51] Int. Cl.⁴ ............................................. A61C 13/22
[52] U.S. Cl. ..................................... 433/171; 433/213; 264/18
[58] Field of Search ............... 433/171, 34, 167, 213, 433/214; 264/16, 17, 18

[56] References Cited

U.S. PATENT DOCUMENTS

| | | | |
|---|---|---|---|
| 2,768,440 | 10/1956 | Elliott | 433/171 |
| 3,621,575 | 11/1971 | Schneider et al. | 433/171 |
| 3,644,996 | 2/1972 | Weinkle | 433/171 |
| 3,667,123 | 6/1972 | Huey | 433/171 |
| 3,839,796 | 10/1974 | Hazar | 433/171 |
| 4,017,971 | 4/1977 | Hazar | 433/171 |
| 4,097,992 | 7/1978 | Hazar | 433/171 |
| 4,247,287 | 1/1981 | Gigante | 433/171 |
| 4,345,900 | 8/1982 | Katz et al. | 433/171 |
| 4,370,133 | 1/1983 | Seempel | 433/171 |
| 4,470,815 | 9/1984 | Hazar | 433/171 |

Primary Examiner—Gene Mancene
Assistant Examiner—James Hakomaki
Attorney, Agent, or Firm—Don J. Flickinger; Jordan M. Meschkow

[57] ABSTRACT

Customized dentures are manufactured by first producing denture bases in one of a plurality of standard sizes each having sockets therein for receiving an array of artificial teeth. Next, an array of artificial teeth removably coupled together by means of a U-shaped appliance which maintains the occlusal aspects of the teeth is positioned in the sockets. Such denture bases which may be wax, uncured synthetic resin or a cured synthetic resin are then shipped and inventoried by a dentist. To fit a particular oral cavity, the dentist first makes an impression of the oral cavity and from that impression upper and lower models are casted. The dentist then selects a denture base having the artificial teeth positioned thereon in one of the standard sizes which most closely accommodates the models. The denture bases are then conformed to the surface contours of the models and the prosthetic teeth are secured in the sockets.

64 Claims, 14 Drawing Figures

CUSTOM DENTURES AND METHOD OF MAKING SAME

CROSS-REFERENCE TO RELATED APPLICATION

This instant application is a continuation-in-part of a co-pending application for U.S. Ser. No. 476,233, filed Mar. 17, 1983, entitled "A Method of Making Custom Dentures and a Dental Module for the Use Therein".

BACKGROUND OF THE INVENTION

1. Field of the Invention

This invention relates generally to custom dentures and, more particularly, to an improved method for the formation and manufacture of custom dentures from synthetic materials.

2. Prior Art

The increasing longevity of individual life spans throughout much of the world accompanied by a heightened awareness of the need to maintain the ability to masticate a variety of foods throughout the individual's lifetime in order to provide for his nutritional, bulk and fiber needs has generated an expanding market for dentures. Over the years a host of different devices and a number of various methods of making dentures from synthetic materials have been utilized.

The early dentures has no palates. Upper and lower plates were little more than narrow rims constructed of wood, ivory and hippopotamus tusks which were whittled and shaped to conform to the approximate contours of the upper and lower ridges of an oral cavity. Patterns of the mouth were made of paper and cloth and were used as guides for fitting. The dentures were held in place by springs arranged in such a fashion as to push the upper rims against the upper ridge and the lower rims against the lower ridge.

Around the beginning of the 19th Century, the art of making plaster casts was developed. Palates were added to the upper plate giving improved retention and function. In the middle of the 19th Century, a composition of amber, linseed oil, guttapercha and sulfur was developed for use as a denture base. However, even with this new material available, denture construction was still tedious and time consuming and, because of this, necessarily expensive. Only the wealthy few could afford the services of a dentist while those of modest means went without.

It was not until vulcanite was successfully developed for a denture base material and porcelein as a material for teeth that dentistry was established as a profession that could serve the needs of the majority of people. Although vulcanite was a remarkable denture material for its time, it left much to be desired asthetically. In an attempt to provide more natural looking dentures, a variety of thermoset and thermoplastic resins were tried and ultimately discarded. These resins included such materials as cellulose nitrate, cellulose acetate, phenol formaldehyde, glycols, caseins, and a great many other materials. As did the rubber materials, some of the plastic resins changed their color, became brittle, or generally lost their form. Finally, in 1933, the use of methyl methacrylate (acrylic) was introduced into the making of dentures and today dominates as the most widely used material in the manufacture of dentures.

Conventionally, dentures are made by first taking impressions of the patient's oral cavity. These impressions are then transported to a dental technician who must make molds and castings individually. Teeth must then be set into the molds in preparation for flasking. Next the flask, containing the molding material and teeth, are compressed under high pressure and cured in hot water tanks. The resulting set of dentures are then removed from the flask, cleaned of excess material and sent back to the dentist for ultimate delivery to the dentist. The dentist must then fit the newly made dentures to the patient making adjustments as required.

This conventional method of manufacturing dentures suffers from several disadvantages. First, the dentures must individually be detailed by dental technicians. Since the dental technician may be in a location remote from the area of the dentist's practice, there exists opportunity for distortions in the construction of the conventional denture since the technician has no knowledge of the peculiarities of the patient's mouth. Additionally, conventional dentures require several visits by the patient in order to develop and fit the dentures properly thus causing inconvenience to the patient and possibly added emotional discomfort. Finally, conventional dentures require from two to four hours of chair time depending upon the specific method being employed by the dentist which is in addition to the several hours of technician time thus adding to the overall cost of the dentures.

SUMMARY OF THE INVENTION

It is an object of the present invention to provide an improved customized denture.

It is a further object of the present invention to provide an improved method of making custom dentures.

It is a still further object of the present invention to provide an improved method of making custom dentures wherein the dentures are the product of a master mold which assures that the anatomical detail are transferred onto each set of dentures thus providing greater cosmetic value.

Yet another object of the present invention is to provide a method of manufacturing custom dentures which requires less time and therefore results in less cost to the patient.

A further object of the present invention is to provide an improved custom denture which is fitted from beginning to end only by the dentist involved who is at all times controlling the development of the denture.

Still another object of the present invention is to provide an improved method of providing custom dentures which requires only a single visit to the dentist.

Yet another object of the present invention is to provide an improved method of manufacturing custom dentures which requires only a single impression of the oral cavity.

A still further object of the present invention is to provide an improved method of providing custom dentures which substantially reduces the amount of time required in a dentist's chair to approximately one hour.

Yet another object of the present invention is to provide an improved method of positioning a plurality of prosthetic teeth in one or more sockets of a denture base.

It is a still further object of the present invention to provide an apparatus for maintaining a plurality of prosthetic teeth in a fixed occlusal relationship.

It is yet another object of the present invention to provide a preliminary denture device of standard dimensions for later adaptation to a cast representation of at least a portion of an individual oral cavity.

According to a broad aspect of the invention there is provided a method for making a denture customized to suit a particular oral cavity which includes manufacturing a denture base in one of a plurality of standard sizes each having at least one socket therein for receiving an array of prosthetic teeth. The array of teeth is positioned in the socket or sockets of the denture base. After the dentist manufactures a representation of his patient's oral cavity, he selects a denture base having the prosthetic teeth positioned therein is one of the plurality of standard sizes which is most closely accommodated by the oral representation. The dentist then conforms the selected denture base to the surface contours of the representation and finally secures the prosthetic within the sockets.

According to a further aspect of the invention there is provided a method of positioning a plurality of prosthetic teeth in at least one socket in a denture base which comprises positioning a plurality of prosthetic teeth in a specific occlusal relationship and providing the plurality of prosthetic teeth with removable appliance means so as to maintain the specific occlusal relationship during subsequent processing.

According to a still further aspect of the present invention there is provided an apparatus for maintaining the plurality of prosthetic teeth in a fixed occlusal relationship for insertion into a plurality of sockets in a denture base which comprises a strip of flexible material having a plurality of receiving curves in a major surface thereof. This strip receives each of the plurality of prosthetic teeth which are maintained in position by an adhesive on the major surface.

According to yet a further aspect of the present invention there is provided a preliminary denture device of standard dimensions for later adaptation to a cast representation of an individual's oral cavity comprising a blank of moldable material conforming to the standard dimensions and formed with at least one recess therein. Artificial teeth are adapted for placement in the one recess, the teeth being placed prior to conforming the denture to a cast representation. Means are provided for contacting the teeth and maintaining the occlusal aspects thereof.

The above and other objects, features and advantages of the present invention will be more clearly understood from the following detailed description taken in conjunction with the accompanying drawings in which:

DESCRIPTION OF THE PREFERRED EMBODIMENT

Figure 1:
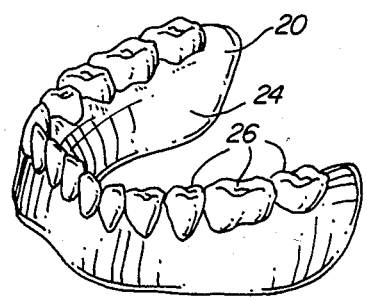
FIGS. 1 and 2 are perspective views of mandibulary and maxilary dentures, respectively, manufactured in accordance with the teachings of the present invention.
Figure 2:
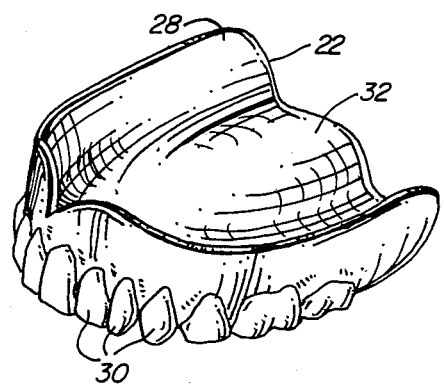

FIGS. 1 and 2 illustrate mandibulary and maxilary dentures 20 and 22 respectively, which are manufactured in accordance with the present invention as can be seen, mandibulary denture 20 includes a base 24 of wax or of a cured or uncured synthetic material and a plurality of artificial or prosthetic teeth 26 fixedly mounted therein. Similarly, maxilary denture 22 includes a base 28 of a wax or of a cured or uncured synthetic material and a plurality of teeth 30. Additionally, base 28 includes a palatal area 32. The mandibulary and maxilary dentures shown in FIGS. 1 and 2 have been conformed to the contours and dimensions of both the endentulus ridge and palatal vault of the individual user. Since the inventive method of manufacturing the dentures shown in FIGS. 1 and 2 is substantially identical for the mandibulary and the maxilary units, the following discussion will be limited to an explanation of the production of a maxilary unit of the type shown in FIG. 2.

The production of the inventive dentures first requires that a completely hand crafted denture including an assembly of artificial teeth with an accurate occlusion including a four and one half inch curve of spee or a flat plane occlusal geometry be constructed. The master denture contains the type of teeth that will be used in the mass produced dentures. A stone model is then constructed by taking an impression of the tissue side of the master denture base including the maxilary and mandibular units. This is accomplished by first coating the denture with a thin coat of petroluem jelly such as Vasoline. A thin strip of metal hereinafter referred to as a frame, is positioned around the denture at a fixed distance from the sides of the denture's periphery. The overlapping area of the metal strip of frame may then be sealed. Next, a heavy mix of dental stone (e.g. of the type available from U.S. Gypsun, Chicago, Ill.) is introduced into the denture so as to fill the denture to its periphery, and the mix of dental stone is slowly vibrated therein. The stone is then smoothed, as for example, with a small spatula, following the contours of the periphery. When the stone is set, it is removed from the metal frame and the denture is removed from the stone. The edges of the stone model may be trimmed; however, the contours of the periphery must be retained. Any voids in the model may then be filled with a small mix of stone.

The next step is the creation of a master mold. First, the master denture is set on the stone model and a thin metal strip is snugly positioned around the base of the stone model. The occlusal surfaces of the posterior teeth and the incisal edge of the anterior teeth are then checked to assure that they are below the top of the frame. If this is not the case, the height of the stone model must be altered on a stone trimmer. The metal form is now sealed. Flexane is slowly poured inside the frame, over the teeth roots and palate of the denture until the frame is filled. The Flexane is allowed to cure at room temperature for approximately twenty-four hours at which time the frame, mantle and master may be removed. The Flexane is available from DEVCON CORPORATION, Danvers, Mass. and its use results in a rubber-like urethane master mold.

It is next necessary to produce a reproduction of the master mold. To accomplish this, a thin metallic strip is positioned around the master mold. Any space around the seam of the metal strip may be sealed with silicone. This comprises another frame.

A set of teeth is inserted into the conforming recess sockets of the master mold of the same type as used in the master denture. The frame is then sealed slab with dental stone and the master mold is placed inside the frame. RTV630 silicone which has been de-aired in a vacuum bell is slowly poured inside the master mold filling the frame to the. The silicone is allowed to cure at room temperature for approximately twenty-four to thirty hours. The resulting silicone reproduction of the master mold may then be removed from the master mold and metal band. RTV is a silicone rubber compound available from General Electric Company, Silicone Products Department, Waterford, N.Y.

FIG. 3 illustrates a maxilary master mold having a palatal area 34 and tooth sockets 36.

A monothane production mold is then fabricated by slowly pouring heated monothane inside the silicone reproduction. The monothane and the silicone reproduction is preheated to approximately 155° F. for a period of one hour in, for example, a preheating oven equipped with a circulating fan. Once inside the silicone mold, the monothane is cured for a minimum of four hours at a temperature not to exceed 275° F. The monothane production mold may then be removed after it has cooled. A monothane suitable for use is a one component polyurethane rubber, ninety to one hundred durometer and available from Indpol of Cucamonga, Calif. The resulting production mold shown in FIG. 4 includes a palatal area 38 and a plurality of projections 40 corresponding in location and position to sockets 36 in the master mold.

Figure 4A:
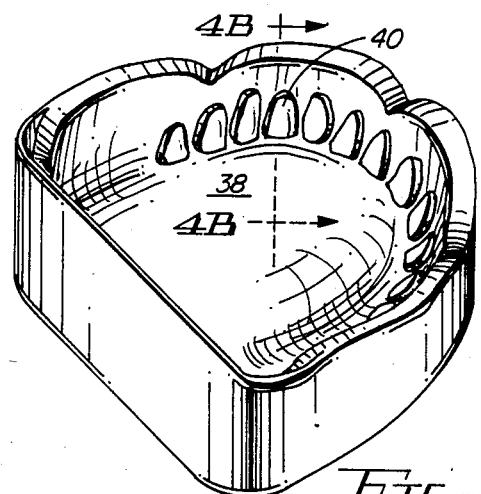
FIGS. 4A and 4B are perspective and cross-sectional views, respectively, of a master mold used in the fabrication of the denture shown in FIG. 2.
Figure 4B:
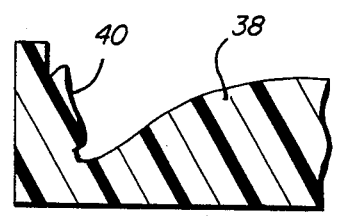
Figure 5:
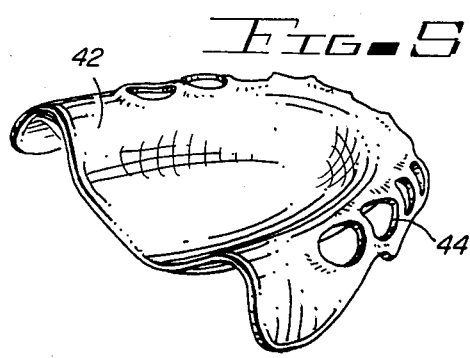
FIGS. 5 and 6 are perspective and frontal views, respectively, of a maxilary denture base having sockets therein produced in accordance with the teachings of the present invention.
Figure 6:
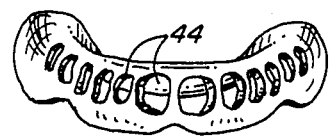

FIGS. 5 and 6 are perspective and frontal views of a maxilary denture base constructed from the production mold shown in FIG. 4. As can be seen, the denture base includes a palatal area 42 and a plurality of tooth sockets 44. It should be understood that these dentures will be reproduced in any of the plurality of standard sizes. Obviously, this requires molds of standard sizes produced from master dentures of standard sizes.

The denture base shown in FIGS. 5 and 6 may be manufactured from a wax material such as paraffin wax compound or other similar compound known in the art; suitable compound is available from Conoco Chemical Company, Houston, Tex. or Pearsall Chemical Company, Houston, Tex., or may be manufactured from a synthetic resin, preferably methyl methacrylate acrylic available from Eschem Company, Essington, Pa. The denture base resulting from use of the synthetic resin may be cured or uncured. To produce a cured pliable denture base, the production mold shown in FIG. 4 is filled with a mixture of methyl methacrylate acrylic resin (for example type #919S0000). A hydraulic press is used to apply from three to four thousand pounds per square inch of pressure on the flask to insure an exact impression of the master denture. The flask or mold is then removed from the hydraulic press and put in a compress and tightened with an impact wrench. The denture base is then cured in a hot water bath having a minimum temperature of 200° F. and preferably 212° F. for approximately one half hour. The soft and flexible denture base is then removed.

To produce an uncured pliable denture base, the production mold is filled with a mixture of, for example, methyl methacrylate acrylic resin, type #139 Standard Denture Polymer that meets ADA specifications, polymerized and formulated to meet the requirements of the dental industry and suitable for conventional flasking and curing in hot water baths. This material is also available from Eschem Company, Essington, Pa. Again, a hydraulic press is used to apply between three thousand and four thousand pounds per square inch pressure on the flask to insure an exact impression of the master denture. The flask is then removed from the hydraulic press, placed in a compress and tightened with an electric impact wrench. The compress and the denture is cooled at approximately 10° F. for approximately twenty four hours. The denture base is then removed.

To produce the wax denture base, the mold is filled with the formulated paraffin and bees wax material which has had its temperature elevated to between 101° F. and 130° F. (preferably 110° F.) at which point it becomes completely moldable. Again a hydraulic press is used to apply pressure on the flask to insure an exact impression of the master denture. The flask is then cooled and the wax denture base is removed.

Figure 7:
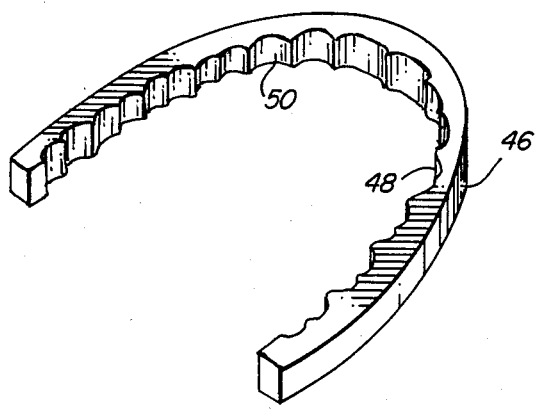
FIG. 7 is a perspective view of a U-shaped appliance for removably securing a plurality of artificial teeth in a fixed occlusal relationship.

The next step in the manufacture of the dentures shown in FIGS. 1 and 2 is the insertion of artificial or prosthetic teeth identical to those in the master denture into sockets 44 of the denture base. This procedure is greatly simplified by interconnecting the artificial teeth by means of, for example, a removable U-shaped flexible and adhesive appliance which maintains the occlusal aspects of the teeth during subsequent processing. Such an appliance is shown in FIG. 7. As can be seen, appliance 46 is provided with a plurality of receiving curves 48 which correspond in contour and position with a front surface of the master mold and therefore are in alignment with the sockets 44 of the denture base shown in FIGS. 5 and 6. A thin layer of adhesive is provided on the inner surface of the appliance which will contact and removably secure the artificial or prosthetic teeth. If desired, the appliance may have a tapered width; i.e. the appliance is wider in its frontal region and tapers towards the ends thereof.

Figure 3A:
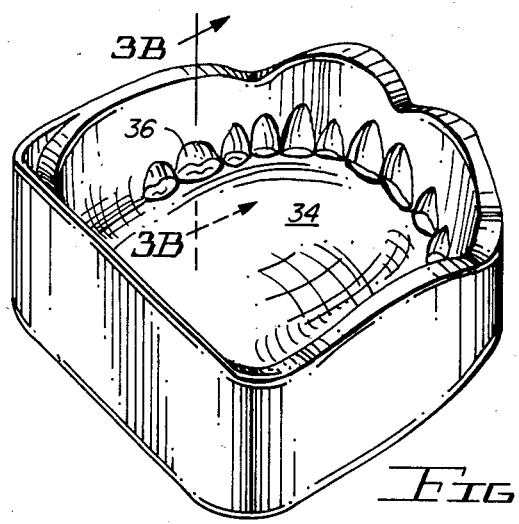
FIGS. 3A and 3B are perspective and cross-sectional views, respectively, of a master mold used in the fabrication of the denture shown in FIG. 2.
Figure 3B:
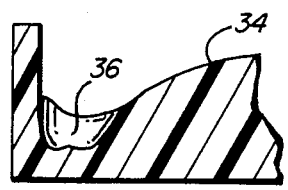
Figure 8:
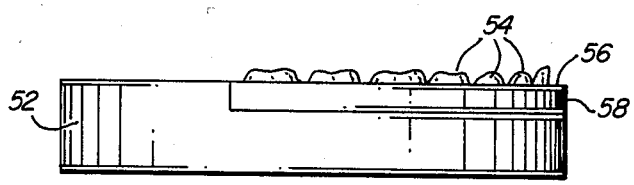
FIG. 8 illustrates the apparatus from which the U-shaped appliance shown in FIG. 7 is produced.

The appliance shown in FIG. 7 may be simply manufactured from a monothane or polyurethane master mold 52 identical to that shown in FIGS. 3A and 3B except that a frontal portion of the mold has been removed such that if artificial teeth 54 were inserted into their corresponding sockets in the mold, they would project a predetermined distance above upper edge 56 of the mold (FIG. 8). Thus, a strip 58 is removed which corresponds to the appliance 46 shown in FIG. 7. The receiving contours are then coated with a pressure sensitive adhesive.

It is next necessary to secure the individual artificial or prosthetic teeth to the receiving curves in the U-shaped appliance. This may be accomplished as follows. First, a third master mold is prepared of the type shown in FIGS. 3A and 3B including sockets or cavities 36 and a frontal portion of the mold is removed such that a portion of the front surface of the prosthetic teeth will be exposed after insertion into the cavities or sockets. Next, the palatal area to the rear of the artificial teeth is built up so as to provide rear support. The artificial or prosthetic teeth are then inserted into the cavities or sockets of this mold and the flexible and adhesive U-shaped appliance is applied to the surfaces of the prosthetic teeth. The prosthetic teeth may now be lifted out of the mold removably secured to the appliance as an array of teeth which is ocluded in accordance with the master denture.

The array of teeth may now be dropped into the sockets of the denture base and, if desired, a portion of the array may be secured to the denture base by applying a small amount of self-curing resin such as oryl acrylic resin.

Figure 9:
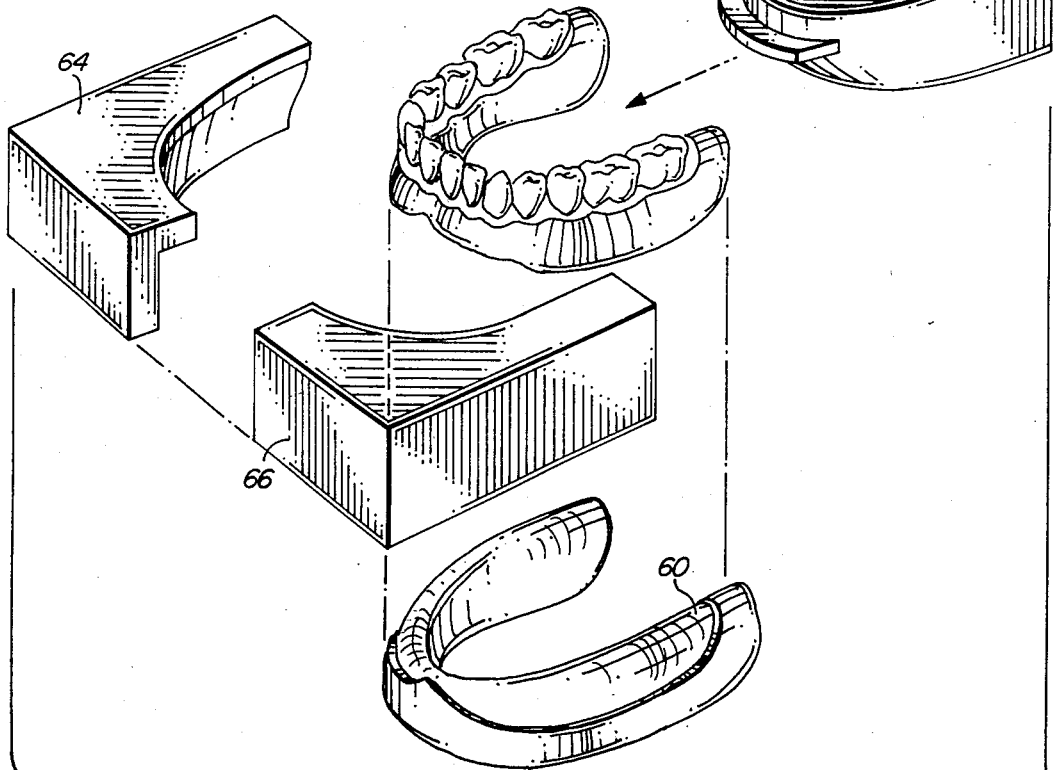
FIGS. 9 and 10 are exploded perspective views illustrating how the dentures shown in FIGS. 1 and 2, respectively, may be packed for shipment.
Figure 10:
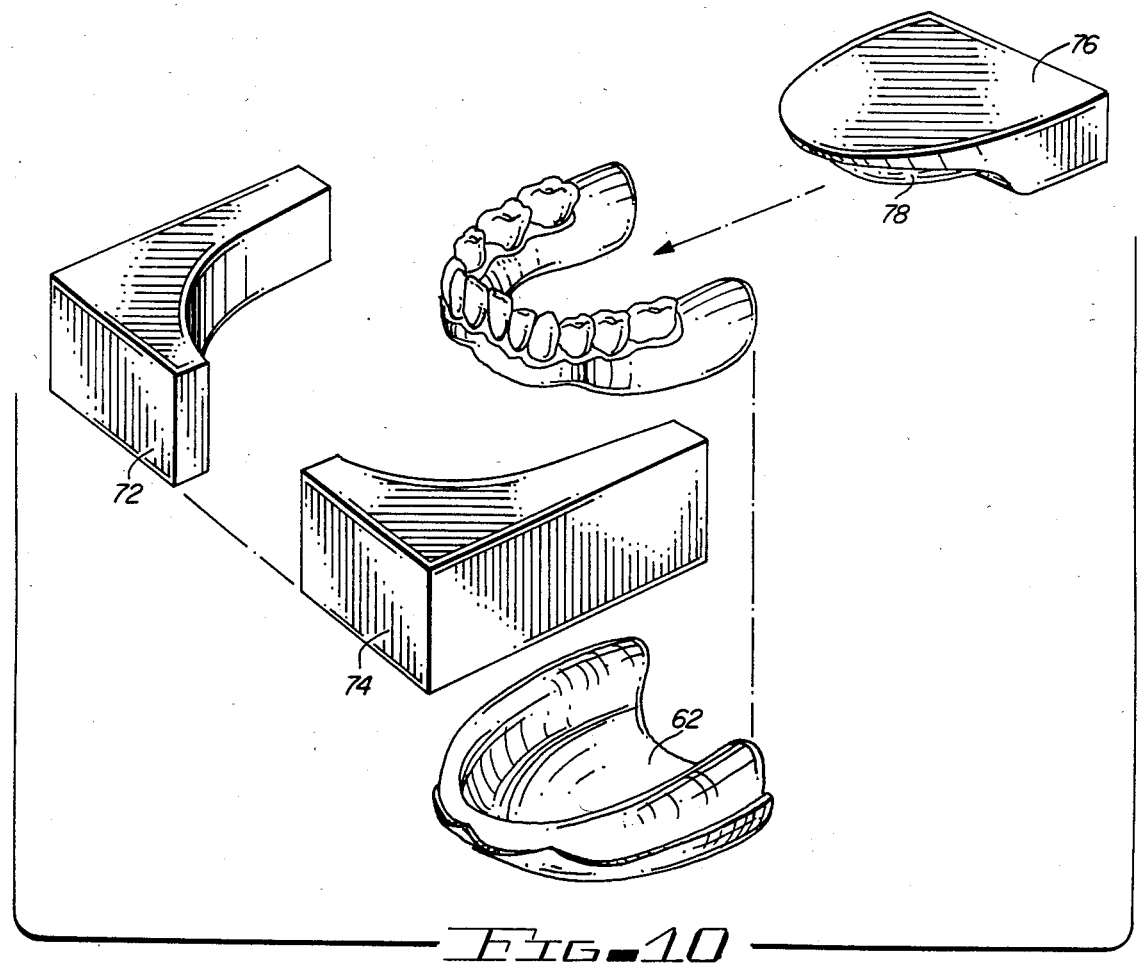

The denture base having the array of teeth positioned thereon is now ready for shipment to a dentist. During storage and shipment, it is necessary that both the denture base and the array of teeth be adequately protected. This may be accomplished by placing both the mandibulary and maxilary denture bases in a carrier 60 and 62 respectively, and then securing the denture base and carrier in a split mold as shown in FIGS. 9 and 10 respectively. In FIG. 9, the split mold is shown as comprising first and second frontal sections 64 and 66, each having an L-shaped cross section and a rearward or palatal section 68 which is equipped with a lip or projection 70 for adequately securing the denture/carrier assembly. The split mold shown in FIG. 10 also comprises first and second frontal portions 72 and 74 and a rearward palatal section 76 having a contoured surface 78.

The split molds shown in FIGS. 9 and 10 may be manufactured from a moldable low density material such as polyester or styrofoam. In the case of uncured acrylic denture bases, it is considered preferable to vacuum pack the denture bases. Having now been properly packed, the denture bases and corresponding arrays of artificial teeth may be shipped to the dentist in a plurality of standard sizes.

In order to provide a specific patient with custom dentures, the dentist first makes an impression of the patient's oral cavity and produces upper and lower casted models from the impression. The dentist further occludes the upper and lower models to establish the occlusal index and derives the occlusal vertical dimension. The dentist then selects a denture base from his inventory of standard size denture bases which most closely accommodates the upper and lower casted models. The denture base selected will have an array of teeth associated therewith as described previously. Each denture is placed on its respective model and the region palate areas are adjusted. The denture base is formed into a closely fitted relationship with the model and the flanges are trimmed to relieve overextension. If the denture base is of the wax variety, the denture base is formed into a closely fitted relationship with the endentulus oral cavity. Next, the wax denture is inserted into a flask and investment casted in the conventional manner.

If the denture base selected is of the uncured acrylic resin type, the prosthetic teeth are secured within the sockets by first applying a layer of uncured acrylic resin on the tissue side of the denture base and then curing the denture base and the layer of uncured acrylic resin so as to secure the teeth. The denture is secured by elevating its temperature (e.g. for example in a hot water bath having a temperature of approximately 212° F. for approximately thirty minutes). The final denture module is produced by trimming excess material from the denture module, removing excess material and polishing the module.

If the selected denture base is of the cured acrylic resin type, the prosthetic teeth are secured by applying a layer of uncured acrylic resin on the tissue side of the denture base and curing the layer of uncured acrylic resin in the manner described above so as to secure the prosthetic teeth.

Regardless of the type of denture base selected, the U-shaped appliance may be removed after the prosthetic teeth are secured to the denture base.

Figure 11:
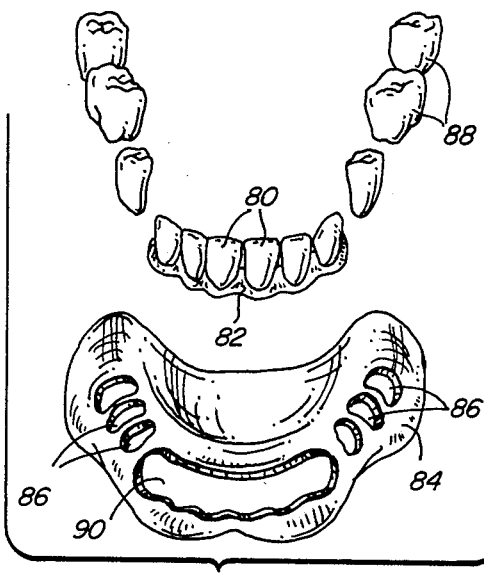
FIGS. 11 and 12 illustrate alternate embodiments of the present invention.
Figure 12:
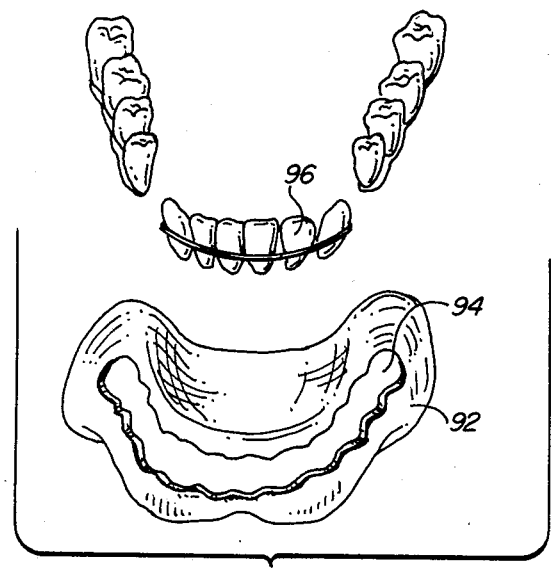

FIGS. 11 and 12 illustrate alternate approaches which utilize partial or completely preformed arrays of teeth. For example, FIG. 11 illustrates a combination of a partial preformed array including a number of individual prosthetic 80 fixedly imbedded in a fully detailed and cured base 82. The preformed array is preferably made of the same material utilized in forming base 84. As shown, base 84 contains a plurality of recesses or sockets 86 for receiving individual teeth 88 along with an extended socket 90 which accommodates base 82 of the fixed array. In FIG. 12, base 92 is molded with a single socket 94 along the exposed surface of the endentulus ridge for receiving an integral or segmented array 96 of prosthetic teeth. In this case, the prosthetic teeth are maintained in fixed relationship by a wire 98 extending internally therethrough (not shown) or by forming the array initially as an integral unit. To provide the dentist with an increased ability to shape the denture for a custom fit, the array 96 can be made in three adjacent segments as shown. This permits the dentist to alter the shape of the endentulus ridge to suit the patient. The integral array prevents lateral adjustment of the anterior portion of the ridge.

The overall or gross dimensions of the human oral cavity vary greatly throughout the bulk of the population. However, the ability to conform the denture in the present process requires only a limited number, typically three, of different sized dental bases be inventoried by the dentist. The versatility of the present method permits the adjustment of the denture to suit the individual's oral cavity dimensions and configuration. This adjustment can be made in a short period of time during a single visit. Thus, a custom denture is provided in a single visit.

The above description is given by way of example only. Changes in form and details may be made by one skilled in the art without departing from the scope of the invention as defined by the appended claims.

I claim:

1. In a method of making a denture customized to suit a particular oral cavity, the steps comprising:
    (a) manufacturing a denture base in one of a plurality of standard sizes and having at least one socket therein for receiving an array of prosthetic teeth;
    (b) positioning said array in said at least one socket;
    (c) manufacturing a representation of said particular oral cavity;
    (d) selecting a denture base having prosthetic teeth positioned therein in one of said plurality of standard sizes which is most closely accommodated by said representation;
    (e) conforming the selected denture base to the surface contours of said representation; and
    (f) securing said prosthetic teeth within said sockets.

2. A method according to claim 1 wherein the step of manufacturing a denture base includes forming a plurality of sockets therein.

3. A method according to claim 2 wherein the step of manufacturing a denture base includes forming one socket therein for each prosthetic tooth to be secured thereon.

4. A method according to claim 3 wherein said step of manufacturing a denture base includes:
  (a) preparing a master denture including teeth secured in a base;
  (b) preparing a master mold from said master denture including cavities therein corresponding in position to the locations of the teeth in said master denture;
  (c) positioning prosthetic teeth in said cavities;
  (d) manufacturing a production mold having protrusions therein corresponding in size, shape and position to said cavities; and
  (e) filling said production mold with a moldable material to form said denture base.

5. A method according to claim 4 wherein said step of manufacturing a denture base includes subjecting said moldable material in said production mold to a pressure of approximately 3,000 psi to 4,000 psi.

6. A method according to claim 4 wherein said step of positioning said array includes the step of interconnecting individual prosthetic teeth.

7. A method according to claim 6 wherein the step of interconnecting includes providing said array with removable appliance means for maintaining the occlusal aspects thereof during subsequent processing.

8. A method according to claim 7 wherein the step of providing removable appliance means includes the step of manufacturing a U-shaped flexible and adhesive appliance having receiving curves in one surface thereof for removably securing a plurality of prosthetic teeth.

9. A method according to claim 8 wherein the step of providing removable appliance means includes the step of manufacturing a U-shaped flexible and adhesive appliance, the major surfaces of which have a tapered width.

10. A method according to claim 9 wherein the step of manufacturing a U-shaped appliance includes:
  (a) preparing a second master mold having said cavities therein, a surface of said second master mold adjacent said cavities contouring the inner proximal surfaces of said array of prosthetic teeth;
  (b) removing a strip of said second master mold including a portion of the surface adjacent said cavities; and
  (c) coating said surface with a pressure sensitive adhesive.

11. A method according to claim 10 wherein the step of interconnecting individual prosthetic teeth further includes securing individual prosthetic teeth to said receiving curves in said one surface.

12. A method according to claim 11 wherein the step of securing individual prosthetic teeth to said receiving curves includes:
  (a) preparing a third master mold including a palatal area and including said cavities;
  (b) removing a portion of the front of said third master mold such that a portion of the front surface of said prosthetic teeth will be exposed after insertion into said cavities;
  (c) building up said palatal area to provide rear support for said prosthetic teeth inserted into said cavities;
  (d) inserting said prosthetic teeth into the cavities of said third master mold;
  (e) applying the flexible and adhesive U-shaped appliance to the surfaces of said prosthetic teeth; and
  (f) lifting the prosthetic teeth as an array on said appliance out of the third master mold occluded in accordance with said master denture.

13. A method according to claim 7 wherein the step of positioning said array in said at least one socket includes inserting said array on said appliance into said at least one socket.

14. A method according to claim 13 wherein the step of positioning further includes securing a portion of said array to said denture base.

15. A method according to claim 14 wherein the step of securing a portion of said array includes applying a small amount of self-curing resin to a portion of said denture base.

16. A method according to claim 15 wherein said self-curing resin is a hard oryl acrylic resin.

17. A method according to claim 13 further comprising the step of packing said denture base and the inserted array of teeth in a split mold for storage and transport.

18. A method according to claim 17 wherein said split mold is made of a moldable low density material.

19. A method according to claim 18 wherein said moldable low density material is polyester.

20. A method according to claim 18 wherein said moldable low density material is styrofoam.

21. A method according to claim 17 wherein said moldable material is an uncured synthetic resin.

22. A method according to claim 21 wherein said synthetic resin is methyl methacrylate acrylic.

23. A method according to claim 21 wherein said denture base and inserted prosthetic teeth are cooled to a temperature lower than ambient prior to packing.

24. A method according to claim 23 wherein said denture base and inserted prosthetic teeth are cooled at approximately 10° F. for approximately 24 hours.

25. A method according to claim 24 wherein said denture base and inserted prosthetic teeth are vacuum packed.

26. A method according to claim 21 further including the step of curing the denture base.

27. A method according to claim 26 wherein the step of curing includes placing the denture base, inserted array of prosthetic teeth and production mold into hot water for a predetermined period of time.

28. A method according to claim 27 wherein the step of curing includes placing the denture base and array of teeth in water having a temperature of at least 200° F. for a period of one-half hour.

29. A method according to claim 28 wherein the denture base and array of teeth are placed in water having a temperature of approximately 212° F.

30. A method according to claim 17 wherein said moldable material is wax.

31. A method according to claim 30 including the step of elevating the temperature of said wax prior to filling said production mold.

32. A method according to claim 31 wherein the wax is elevated in temperature to between 100° F. and 130° F.

33. A method according to claim 32 wherein the wax is heated to approximately 110° F.

34. A method according to claim 17 wherein the step of manufacturing a representation of said particular oral cavity includes:
  (a) making an impression of said oral cavity; and
  (b) making upper and lower casted models from said impression.

35. A method according to claim 34 further including:
(a) occluding the upper and lower models to establish the occlusal index; and
(b) deriving the occlusal vertical dimension.

36. A method according to claim 34 wherein the step of selecting a denture base includes selecting a standard size upper and lower denture base having prosthetic teeth positioned therein which are most closely accommodated by said upper and lower casted models.

37. A method according to claim 36 wherein the step of conforming includes:
(a) placing each denture base on its respective model;
(b) adjusting the ridge and palate areas;
(c) forming the denture base into a closely fitted relationship with the model; and
(d) trimming the flanges to relieve overextension.

38. A method according to claim 36 wherein the step of conforming includes:
(a) placing each denture base on its respective model;
(b) adjusting the rigid palate areas;
(c) forming the denture base into a closely fitted relationship with the model;
(d) trimming the flanges to relieve over extension; and
(e) forming the base into a closely fitted relationship with the endentulus oral cavity.

39. A method according to claim 37 wherein said moldable material is uncured acrylic resin and wherein the step of securing the prosthetic teeth within said sockets includes:
(a) applying a layer of uncured acrylic resin on the tissue side of the denture base; and
(b) curing the denture base and layer of uncured acrylic resin to secure said prosthetic teeth and form a denture module.

40. A method according to claim 38 wherein the wax denture base and its associated artificial teeth are inserted into a flask and investment casted.

41. A method according to claim 39 further including:
(a) trimming excess material from the denture module;
(b) removing excess material from said denture module; and
(c) polishing said denture module.

42. A method according to claim 39 wherein the step of curing the denture base and applied layer of uncured acrylic resin includes placing the denture base in a hot water bath having a temperature of approximately 212° F. for approximately 30 minutes.

43. A method according to claim 37 wherein said denture base is cured acrylic resin and wherein the step of securing the prosthetic teeth within said sockets includes:
(a) applying a layer of uncured acrylic resin on the tissue side of the denture base; and
(b) curing the layer of uncured acrylic resin to secure said prosthetic teeth and form a denture module.

44. A method of positioning a plurality of prosthetic teeth in at least one socket of a denture base, the steps comprising:
(a) positioning said plurality of prosthetic teeth in a specific occlusal relationship; and
(b) providing said plurality of prosthetic teeth with removable appliance means to maintain the specific occlusal relationship during subsequent processing.

45. A method according to claim 44 wherein the step of providing removable appliance means includes the step of manufacturing a U-shaped flexible and adhesive appliance having receiving curves in one surface thereof for removably securing said plurality of prosthetic teeth.

46. A method according to claim 45 wherein the step of providing removable appliance means includes the step of manufacturing a U-shaped flexible and adhesive appliance, the major surfaces of which have a tapered width.

47. A method according to claim 46 wherein the step of manufacturing a U-shaped appliance includes:
(a) preparing a master mold of an oral cavity having cavities therein corresponding to the size, shape and location of said plurality of prosthetic teeth, a surface of said master mold adjacent said inner proximal surfaces of said plurality of prosthetic teeth;
(b) removing a strip of said master mold including a portion of the surface adjacent said cavities; and
(c) coating said surface with a pressure sensitive adhesive.

48. A method according to claim 47 further including the step of securing individual prosthetic teeth to said receiving curves.

49. A method according to claim 48 wherein the step of securing individual prosthetic teeth to said receiving curves includes:
(a) preparing a second master mold including a palatal area and including said cavities;
(b) removing a portion of the front of said second master mold such that a portion of the front surface of said prosthetic teeth will be exposed after insertion into said cavities;
(c) building up said palatal area to provide rear support for said prosthetic teeth inserted into said cavities;
(d) inserting the prosthetic teeth into the cavities of said second mold;
(e) applying the flexible and adhesive U-shaped appliance to the exposed surfaces of said prosthetic teeth; and
(f) lifting the prosthetic teeth as an array on said appliance out of the second master mold occluded in said specific occlusal relationship.

50. An apparatus for maintaining a plurality of prosthetic teeth in a fixed occlusal relationship for insertion into a plurality of sockets in a denture base comprising:
(a) a strip of flexible material;
(b) a plurality of receiving curves in a major surface of said strip for receiving each of said plurality of prosthetic teeth; and
(c) adhesive means on said major surface for securing said plurality of prosthetic teeth.

51. An apparatus according to claim 50 wherein said strip has a width which diminishes from its center toward the ends thereof.

52. An apparatus according to claim 51 wherein said strip is U-shaped.

53. An apparatus according to claim 52 wherein said strip is made of monothane.

54. An apparatus according to claim 52 wherein said strip is made of polyester.

55. An apparatus according to claim 52 wherein said strip is made of a moldable metal.

56. An apparatus according to claim 55 wherein said moldable metal is lead.

57. A preliminary denture device of standard dimensions for later adaptation to a cast representation of a least a portion of an individual oral cavity, comprising:
(a) a blank of moldable material conforming to said standard dimensions and formed with at least one recess therein;
(b) artificial teeth means adapted for placement in said at least one recess, said teeth means being placed in said recess prior to conforming said denture device to said cast representation; and
(c) first means for contacting said teeth means and maintaining the occlusal aspects thereof.

58. A preliminary denture device according to claim 57 further comprising a support mold having said general dimensions for receiving said blank thereon.

59. A preliminary denture device according to claim 58 wherein said support mold comprises a split mold for maintaining the configuration of the surface of said blank and teeth means during storage and transport.

60. A preliminary denture device according to claim 57 wherein said artificial teeth means includes a plurality of individual teeth configured in a fixed array.

61. A preliminary denture device according to claim 57 wherein said moldable material is an uncured synthetic resin.

62. A preliminary denture device according to claim 57 wherein said moldable material is wax.

63. A preliminary denture device according to claim 57 wherein said moldable material is a cured synthetic resin.

64. A preliminary denture device according to claim 57 wherein said blank has a plurality of recesses therein each for receiving individual prosthetic teeth.

* * * * *